(12) United States Patent
Winfried et al.

(10) Patent No.: US 8,637,327 B2
(45) Date of Patent: Jan. 28, 2014

(54) METHOD FOR OPTIMIZING AUTOMATIC FLUORESCENCE PATTERN RECOGNITION IN IMMUNODIAGNOSIS

(75) Inventors: Stöcker Winfried, Gross Grönau (DE); Hendrik Fauer, Stockelsdorf (DE); Christopher Krause, Lüberck (DE); Erhardt Barth, Ratekau/ovendorf (DE); Thomas Martinetz, Lübeck (DE)

(73) Assignee: Euroimmun Medizinische Labordiagnostika AG (DE)

( * ) Notice: Subject to any disclaimer, the term of this patent is extended or adjusted under 35 U.S.C. 154(b) by 789 days.

(21) Appl. No.: 12/304,059

(22) PCT Filed: Jun. 1, 2007

(86) PCT No.: PCT/EP2007/004897
§ 371 (c)(1),
(2), (4) Date: Oct. 22, 2009

(87) PCT Pub. No.: WO2007/140952
PCT Pub. Date: Dec. 13, 2007

(65) Prior Publication Data
US 2010/0047811 A1 Feb. 25, 2010

(30) Foreign Application Priority Data

Jun. 9, 2006 (DE) .......................... 10 2006 027 516

(51) Int. Cl.
*G01N 33/533* (2006.01)
*G01N 1/30* (2006.01)
*G01N 21/00* (2006.01)

(52) U.S. Cl.
USPC ............... 436/546; 436/56; 436/63; 436/164; 436/166; 436/171; 436/172; 436/175; 435/2; 435/7.1; 435/7.2; 435/7.21; 435/40.5; 435/40.52

(58) Field of Classification Search
USPC .......... 435/7.21, 40.5, 40.52, 371, 2, 7.1, 7.2; 436/546, 56, 63, 64, 164, 166, 171, 436/172, 175
See application file for complete search history.

(56) References Cited

U.S. PATENT DOCUMENTS

2002/0186875 A1* 12/2002 Burmer et al. ................ 382/133

OTHER PUBLICATIONS

Sack et al. Computer-assisted classification of HEp-2 immunofluorescence patterns in autoimmune diagnostics. Autoimmunity Reviews 2: 298-304 (2003).*
Kollner et al. Fluorescence Pattern Recognition for ultrasensitive molecule identification: comparison of experimental data and theoretical approximations, Chemical Physics Letters 250: 355-360 (Mar. 1, 1996).*

* cited by examiner

*Primary Examiner* — Gail R Gabel
(74) *Attorney, Agent, or Firm* — Hovey Williams LLP

(57) ABSTRACT

The invention relates to a method for optimizing the automatic fluorescence pattern recognition in immunodiagnosis. In this method, in addition to or together with the fluorescence dye, one or more other indicator dyes for the identification of relevant structures are incubated before an image is taken with a camera.

3 Claims, No Drawings

METHOD FOR OPTIMIZING AUTOMATIC FLUORESCENCE PATTERN RECOGNITION IN IMMUNODIAGNOSIS

CROSS-REFERENCE TO RELATED APPLICATIONS

This is a National Phase Application pursuant to 37 C.F.R. §371 of International Application No. PCT/EP2007/004897, filed Jun. 1, 2007, claiming priority from German Application No. DE 10 2006 027 516.0, filed Jun. 9, 2006, the entire disclosures of which are hereby incorporated by reference herein.

BACKGROUND OF THE INVENTION

1. Field of the Invention

The invention relates to a method for optimizing the automatic fluorescence pattern recognition in immunodiagnosis. It serves for optimizing reliability and accuracy in computer-aided automatic interpretation of fluorescence patterns in immunodiagnosis.

2. Discussion of the Prior Art

In the indirect immunofluorescence test (IIFT), the results are generally evaluated visually per field by assessing the fluorescence pattern or the image under a microscope. Alternatively, or in support of this, automated methods can be employed for pattern classification.

In medical immunodiagnosis, the detection of antibodies in a patient's serum is an indication of a specific clinical picture. Cells and tissue sections serve here as antigen substrates. The sample material from the patient (e.g. serum diluted with aqueous potassium salt solution) is incubated for testing with these antigen substrates. The antibodies that are to be detected, if present in the serum, bind to the solid-phase-bound antigens. Bound antibodies are made visible under the microscope by a fluorescence dye. Depending on the particular antibody, characteristic patterns become visible.

Antinuclear antibodies (ANA) are often tested on human epithelial cells (HEP), primate livers and other tissues, for example in patients with various rheumatic diseases. Fifty different antinuclear antibodies can be identified in this way. For example, antibodies against nDNS (*lupus erythematosus*), SLE, against centromeres (forms of progressive systemic sclerosis) and against nuclear dots (liver cirrhosis). In addition, the cytoplasm can also fluoresce, for example if antimitochondrial antibodies are present (diagnosis: primary biliary cirrhosis (PBC)).

It is equally possible for bacteria or virus-infected cells to be used as substrate and for the corresponding infectious diseases to be diagnosed in this way. The diagnosis with infected cells or viruses represents a highly valid diagnosis.

The immunofluorescence technique has many advantages. For example, many parameters are investigated, and many different antibodies are often identified with one substrate. The antigens are directly available, whereas in biochemical methods they first have to be isolated and bound. For this reason, the antigens are present in the best possible native form, and the antibody diagnosis with the immunofluorescence technique is in many cases particularly competent in diagnostic terms. Because of differences in the fluorescence patterns, it is also possible for specific and non-specific reactions to be differentiated particularly clearly from one another. By contrast, biochemical methods only indicate that a reaction has taken place, without the possibility of assessing its relevance, since specific reactions cannot be distinguished from non-specific reactions, something that is often done at a stroke in immunofluorescence by viewing in a microscope.

However, the fluorescence technique cannot be used willingly everywhere as a mass testing method. The evaluation of the fluorescence images is usually done visually and requires highly trained personnel, it is time-consuming, and one of its main weaknesses lies in the subjectivity of the assessment. Because of these disadvantages, work has for some time been carried out on automating the pattern recognition in order to make this process more efficient, more objective and more reliable.

The automatic computer-aided evaluation of fluorescence images takes place in several steps. These generally involve imaging, image processing, feature extraction and classification. The classification of the fluorescence images is done by allocating defined image features to classic features of fluorescence patterns. The occasional presence of several antibodies within the patient sample that is to be examined leads to a large number of possible mixed patterns. In the classification, however, the basic patterns from which the mixed forms are composed should be defined in order to determine all identifiable antibodies.

A generally recognized automated analysis of fluorescence images, as is described in the patent DE19801400 for example, has not as yet become widely accepted. This is due in particular to the fact that the quality of the automatic classification, characterized by the statistical parameters of sensitivity, specificity, relevance, segregation, correct classification rate and false classification rate, does not allow the automatic classification to form a basis for a medical diagnosis. The weaknesses of the existing automatic methods lie in two sets of circumstances:

1. On the one hand, the classification of the fluorescence patterns is based on a preceding feature extraction without the application of a permanently effective method for identification of relevant structures in the fluorescence image.
2. On the other hand, the evaluation of the extracted image features is carried out in the form of a hierarchical decision tree. The path to the end result is dependent on each branch directed away from the individual decision that is made. If one of these individual decisions is made incorrectly, this leads to an end result that is generally false.

SUMMARY

The object of the invention is to improve the automatic classification of fluorescence patterns in terms of the statistically relevant parameters, such as sensitivity, specificity, relevance, segregation, correct classification rate and false classification rate.

The solution to this object is achieved by a method for optimizing the automatic fluorescence pattern recognition in immunodiagnosis.

This ensures that the relevant structures for examining the fluorescence patterns generated by specific dyes, for example fluorescein, can be reliably located on the images and can be extracted in individual images, and that the results cannot be rendered false by individual incorrect interpretations.

DETAILED DESCRIPTION OF THE PREFERRED EMBODIMENTS

The computer-aided, automatic classification of fluorescence patterns is thus optimized in terms of the number of distinguishable patterns and in terms of the quality of the pattern identification. Statistically relevant parameters for the quality in this context are sensitivity, specificity, relevance, segregation, correct classification rate and false classification rate.

The number of distinguishable patterns and the statistical parameters characterizing the quality can be improved by 1. marking relevant structures with the aid of additional dyes in order to be able to identify them with the same high level of reliability, independently of the expressiveness of the fluorescence pattern,
2. extending the method of evaluation of the fluorescence patterns caused by the specific marker dye fluorescein to a large number of relevant structures on different tissue sections, infected cells, non-infected cells and smears of bacteria, fungi or parasites, with subsequent automatic validation of the individual classification results determined for each structure against a results matrix that contains valid results combinations.

In addition to or together with the fluorescence dye, one or more other indicator dyes for the localization of relevant structures are incubated before an image is taken with a camera.

These indicator dyes can be used on tissue sections, infected cells, non-infected cells and smears of bacteria, fungi or parasites in order to support an automatic image evaluation.

It has of course already been proposed to use dual fluorescence techniques, for example by marking the islet cells of the pancreas with rhodamine-coupled antibodies in order to locate them under green excitation and red evaluation. In a second step, the filter would then be changed, and the fluorescence image of the specific patient antibody would be analyzed under blue excitation and green evaluation. This described method of dual fluorescence, however, involves considerable outlay (dye-coupled antibodies against the antigens to be examined are required) for precisely staining the diagnostic target structure, which is too complicated for automated image evaluation, requires the use of two different filter systems in succession, and can lead to the end result being rendered false, since the localization of the islets of the pancreas involves the same biochemical principle as is used in the specific reaction: The antibody used for the localization reaction competes with the antibody of the sample to be examined and thereby reduces the specific signal.

For the automated image evaluation, a dye is used which, independently of the nature of the diagnostic question, stains certain relevant structures on tissue sections, infected cells, non-infected cells and smears of bacteria, fungi or parasites. (Virus or bacteria localization may involve the use of antibodies against determinants that are not diagnostically relevant, e.g. p41 of *Borrelia*). The distribution of the indicator dyes and of the specific fluorescence dyes does not have to agree, although it may well do so.

In the identification of relevant structures with the aid of indicator dyes, use is made of the property of certain dyes, for example propidium iodide, to bind particularly strongly, or exclusively, to certain molecules, for example nucleic acids. By means of propidium iodide, the nuclei, the nucleoli and the chromosome region of cells in the mitotic stage are very clearly marked.

The indicator dyes that are used must be visible on the fluorescence image in their own colour channels. If necessary, several images can also be taken using different filter systems and can then be further processed jointly. Depending on the choice of the indicator dye, the latter can work into the colour channel of the fluorescence dye and must be calculated out from this proportionately. This is done using fixed algorithms or using calibration images. For the generation of calibration images, only the indicator dye is incubated on a slide, without fluorescence dye. The intensity of the colouring in the colour channel of the fluorescence dye not present is to be determined as a function of the colour intensity of the indicator dye and can be presented in a histogram of the recorded microscopic image. The determined colour value in the colour channel of the fluorescence dye is subtracted in the fluorescence patterns according to the associated colour intensity of the indicator dye.

The use of indicator dyes permits reliable identification of relevant tissue or cell structures independently of the fluorescence pattern. In this way, their specific features can be safely extracted in the colour channel of the fluorescence dye in each case.

The different cell types, cell cycle stages or tissue sections react differently depending on the antibody. The totality of the reactions is characteristic for each fluorescence pattern. For example, for differentiating between the fluorescence patterns of antibodies against SSA,B and RNP/SM in the diagnosis of antinuclear antibodies (ANA diagnosis), a characteristic is that the liver cell nuclei in RNP/SM have about the same brightness and in SSA,B fluoresce much more weakly or do not fluoresce compared to the HEP cells. Thus, fluorescence patterns that appear partially the same or similar can be clearly differentiated by taking into consideration differences on other tissue or structures.

To make use of this knowledge for computer-aided fluorescence image analysis and to make the pattern classification robust against individual incorrect allocations, a large number of different structures from tissue sections, infected cells, non-infected cells and smears of bacteria, fungi or parasites are examined by the method described below using a results matrix that contains valid results combinations.

The fluorescence images are divided into groups of individual images of similar relevant structures. These groups contain for example only the chromosome regions of cells in the development stage of mitosis (mitotic cells) or only the nucleoli of interphase cells or only the nuclei of liver tissue sections, etc. For these groups of individual images, quantifiable image features are extracted by means of standard methods of image processing, such as granulometry, grey-scale matrix. By means of classification against the image features of groups of corresponding structures from known fluorescence patterns, a group classification result in the form of a fluorescence pattern allocation is obtained for each group of relevant structures.

The individual group results are then validated against one another on the basis of a three-dimensional property matrix. This property matrix contains for each group (dimension 1) allocations of similar fluorescence patterns (dimension 2) taking into account the fluorescence brightness (dimension 3). In these allocations it must be ensured that an unequivocal end result can always be found.

In the first step, the brightness level of the fluorescence is determined on the images to be analyzed. This is done by evaluating the brightness of a result group suitable for this. With the determined value of the brightness level for this results group, an unambiguous element of the property matrix as entry point and reference point is obtained. A prerequisite for carrying out a brightness evaluation is standardized conditions in the incubation and in the image recording. This particularly concerns incubation temperature and time, and the lighting time, if the dye can fade.

In the second step, the other group results are compared with the results stored for the determined brightness level in the property matrix. This comparison is carried out with reference to the fluorescence pattern allocation and the fluorescence brightness. Similar and therefore possibly also correct results are determined for each group result.

In the third step, the found quantities of results are coordinated and unsuitable combinations are set aside and an unequivocal end result is determined.

This method makes the system robust against incorrect classifications of individual examined image structures.

In summary, it may be stated that, by means of the (fluorescence pattern independent) identification of relevant structures with the aid of easy to handle dyes, the extension of the method of fluorescence pattern evaluation to a large number of relevant structures in tissue sections, infected cells, non-infected cells and smears of bacteria, fungi or parasites, the classification of groups of relevant structures in the form of fluorescence pattern allocation to each group and the common validation of the group results against a three-dimensional results matrix, it is possible to significantly improve the quality of the automatic classification characterized by different statistical parameters.

The invention claimed is:

1. A method for optimizing the automatic fluorescence pattern recognition in immunodiagnosis, said method comprising the steps of:
   a) incubating a test field which includes a first amount of one or more indicator dyes formulated for the identification of selected structures of an organic material, a fluorescence dye for identification of at least one antibody, and the organic material,
   b) viewing the incubated test field with a camera to generate a first colour image having a first set of colour channels associated with the one or more indicator dyes and the fluorescence dye, each of said first colour channels having a corresponding colour intensity, wherein the one or more indicator dyes are visible in the first colour image in one or more of the first colour channels,
   c) differentially identifying in the first colour image the one or more indicator dyes and the fluorescence dye by the first colour channels, wherein the first colour channels include a detection colour channel associated with the fluorescence dye and thereby presenting a total detection colour intensity associated with the test field, and
   d) compensating for an interference effect of the one or more indicator dyes on the detection colour channel of the first colour image, including the steps of:
   e) incubating a calibration field comprising a second amount of the one or more indicator dyes without fluorescence dye,
   f) determining the amount of the interference of the one or more indicator dyes on the detection colour channel of the first colour image by viewing the incubated calibration field to generate a second colour image having a second set of colour channels, wherein the second colour channels include an indicator colour channel corresponding to the detection colour channel of the first colour image and having an indicator colour intensity that is the amount of interference of the one or more indicator dyes on the detection colour channel of the first colour image, and
   g) prior to the automatic fluorescence pattern recognition, correcting the detection colour channel presenting the total detection color intensity of the first colour image by the amount of the measured interference of the indicator dye by subtracting the indicator colour intensity obtained in the calibration field from the total detection colour intensity.

2. The optimization method as claimed in claim 1, said method further including the steps of extracting one or more fluorescence patterns and storing each pattern in a results matrix in which analogous patterns are stored.

3. The optimization method as claimed in claim 2, said method further including the steps of determining a pattern brightness for each fluorescence pattern and storing each pattern brightness in the results matrix.

* * * * *